United States Patent [19]

Hardham et al.

[11] Patent Number: 5,817,472
[45] Date of Patent: Oct. 6, 1998

[54] DETECTION OF MOTILE FUNGAL ZOOSPORES IN A SAMPLE

[75] Inventors: Adrienne Ruth Hardham, Kambah; David Miles Cahill, Deakin, both of Australia

[73] Assignee: The Australian National University, Australian Capital Territory, Australia

[21] Appl. No.: 403,851

[22] PCT Filed: Sep. 22, 1993

[86] PCT No.: PCT/AU93/00487

§ 371 Date: Jun. 9, 1995

§ 102(e) Date: Jun. 9, 1995

[87] PCT Pub. No.: WO94/08042

PCT Pub. Date: Apr. 14, 1994

[30] Foreign Application Priority Data

Sep. 25, 1992 [AU] Australia .............................. PL4971/92

[51] Int. Cl.[6] .......................... G01N 33/53; G01N 33/569
[52] U.S. Cl. ........................ 435/7.31; 435/7.2; 435/7.32; 435/7.35; 435/29; 435/287.2; 530/388.5
[58] Field of Search ................................ 435/287.2, 287, 435/29, 7.35, 7.32, 7.2, 7.31; 530/388.5

[56] References Cited

U.S. PATENT DOCUMENTS

| | | | |
|---|---|---|---|
| 4,563,418 | 1/1986 | Ward, Jr. | 435/7 |
| 4,732,155 | 3/1988 | Zetter et al. | 128/630 |
| 4,845,197 | 7/1989 | Petersen et al. | 530/387 |
| 5,023,173 | 6/1991 | Horwitz | 435/29 |
| 5,132,229 | 7/1992 | Ward, Jr. | 435/288 |
| 5,366,508 | 11/1994 | Brekke | 623/16 |
| 5,415,997 | 5/1995 | Atrache et al. | 435/7.35 |
| 5,460,945 | 10/1995 | Springer et al. | 435/7.24 |
| 5,536,501 | 7/1996 | Emerson et al. | 424/405 |
| 5,683,459 | 11/1997 | Brekke | 623/16 |
| 5,744,366 | 4/1998 | Kricka et al. | 436/63 |

FOREIGN PATENT DOCUMENTS

| | | |
|---|---|---|
| 61141 | 3/1982 | European Pat. Off. . |
| 214340 | 3/1987 | European Pat. Off. . |

OTHER PUBLICATIONS

Experimental Mycology vol. 8, pp. 238–244, 1984, "A Method for Estimating lectin binding to fungal zoospores & cysts" Mary L. Williams (et al.) whole document.

Ragupathi, G et al; Hindustan Antibiot. Bull. (India) Feb.–May 1992, (34) (1–2), pp. 6–12 (abstract).

Ali–Shtayeh, M.S. et al; Plant Disease, Mar. 1991, pp. 305–311.

Halsall, D.M; Canadian J. of Microbiology, vol. 22(3), pp. 409–422 1976 (abstract).

Khew, K.L et al; Phytopathology, vol. 63(12), pp. 1511–1517, 1973.

Halsall, DM et al, Can. J. Microbiol, vol. 22(3), pp. 409–422, 1976 (Full Article).

Segall, JE et al, J. Cell Biol., vol. 104, Jan. 1987, pp. 151–161.

Mansfield, P.J. et al. J. Cell Biol., vol. III, (6 pt 2), Dec. 1990, pp. 3077–3086.

Benson, Plant Disease, vol. 75(5) pp. 478–482, 1991.

Mullen et al, 1989, (Abs) Phytopathology vol. 79:1139, #33.

Hardham A.R. et al, Exp. Mycol. 9(3) 1985, pp. 264–268.

MacDonald, J.D et al, Phytopathology, vol. 69(5) pp. 436–441, 1979.

Yuen, GY et al, Plant Disease, 1993, v77, N7 (Jul) pp. 692–698.

Kelleher, M. et al, Phys. and Mol. Plant Pathology, 1990, v37, N5, pp. 377–387.

*Primary Examiner*—James C. Housel
*Assistant Examiner*—Ginny Allen Portner
*Attorney, Agent, or Firm*—Bacon & Thomas

[57] ABSTRACT

A method for detecting motile organisms, particularly zoospores of *Phytophthora cinnamomi* in a sample comprises contacting the sample with a solid support in a medium in which the organisms are motile, the solid support being, or being treated with, a chemotactic and/or electrotactic attractant for the organisms, and subsequently detecting organisms attracted to the solid support by immunoassay.

20 Claims, No Drawings

DETECTION OF MOTILE FUNGAL ZOOSPORES IN A SAMPLE

FIELD OF THE INVENTION

This invention relates to the detection of motile organisms in a sample, and to a device for use in this method. The method is particularly, but not exclusively, directed to the detection of zoospores of the pathogenic fungus *Phytophthora cinnamomi*. More generally, the method extends to the detection of other organisms that produce motile cells, including bacteria, fungi, algae and protozoa.

BACKGROUND OF THE INVENTION

*Phytophthora cinnamomi* Rands is one of the most important plant pathogens found throughout the tropical and temperate zones (34,36). It affects an increasingly diverse range of species from a wide variety of plant families (35). Hosts include economically important horticultural crops such as avocado, pineapple and macadamia, ornamental species and several valuable timber species. Effects of this fungus on the endemic flora of southeastern Australia and the southwestern part of Western Australia, where some plant species are on the brink of extinction are devastating examples of the impact of an introduced pathogen on a flora composed of many susceptible species (31,34,35). Control of this pathogen and improved understanding of its biology must be based in part on information on the location and density of inoculum in soil. To date, and depending on the method used, this has required relatively difficult and time-consuming procedures to first isolate and then identify *P. cinnamomi* from soil. It is possible to isolate and identify *P. cinnamomi* within 2–3 days (13) but many procedures have used baiting of soil samples for up to 7–10 days followed by plating of the infected bait onto one or more selective media. After several days growth on the selective medium it is necessary for identification to be carried out by someone familiar with Phytophthora taxonomy (14,33).

Currently, the most versatile and useful diagnostic assays are those based on antibodies which specifically recognise the target organism. These assays have been used with great success with plant viral and bacterial diseases (16) and also plant diseases caused by a range of fungi (9). Polyclonal antibodies have been used for the detection of *P. cinnamomi*. Antibodies were produced that permitted detection of chlamydospores of *P. cinnamomi* in soil, but the assay suffered from high background binding of the antibodies to soil particles and lacked specifies-specificity (24). Similar procedures were used to produce antibodies that labelled Phytophthora zoospore cysts and germ tubes, but again these were not species-specific (24). Several immunoassays were developed for a number of important plant pathogens including Phytophthora (27). For example, monoclonal antibodies were used to detect cysts of Phytophthora and Phythium collected from irrigation water on filter pads (1). These assays all have been based on the use of fungal mycelium or mycelial fractions as the immunogen but have also shown considerable lack of specificity. A collection of monoclonal antibodies raised to aldehyde-fixed zoospores of *P. cinnamomi* which, in preliminary studies, showed genus-, species- and isolate-specificities (18), have great potential for the development of a species-specific immunodiagnostic test for *P. cinnamomi*.

It is one object of the present invention to provide a simple, rapid "dipstick" diagnostic immunoassay which in one embodiment, enables the detection and quantitation of *P. cinnamomi* in soil within 1–2 days. A diagnostic immunoassay of this type is based on an antigen absorbed by, or a capture antibody adsorbed to, a dipstick. These assays involve movement of the dipstick from the test solution through solutions containing a labelled antibody and then into a final solution that allows visualisation of bound antibody. This form of immunoassay has been used successfully to detect several plant pathogens (5,10,11,26) and forms the basis of many medical diagnostic assays (21,32). The great advantages of the dipstick-type assays over other antibody-based assays are that they can be carried out quickly, cheaply and without specialised instrumentation, and a reliable diagnosis can be performed by unskilled workers.

Many organisms are able to detect chemical and electrical gradients, and can actively move towards the source of the gradient, finally adhering to the source. These forms of movement are called chemotaxis and electrotaxis, respectively, and the method of the present invention utilises the chemotactic and/or electrotactic ability of organisms.

It is well documented in the literature that a number of compounds act as chemoattractants for motile bacteria, algal, fungal or animal cells. The present inventors have confirmed and extended studies of chemoattraction of zoospores of Phytophthora species and have determined that the amino acids aspartate, glutamate and asparagine as well as a variety of other compounds are strong attractants of these cells. The inventors have also found that when a solid surface such as a filter or membrane is coated with these compounds, or when the compounds are absorbed by a permeable surface, the slow release of the compounds causes the fungal zoospores to swim up to and adhere to the surface. Materials that have been used successfully include nitrocellulose (Bio-Rad Laboratories), nucleopore filter (Gelman), filter paper (#1, Whatman International) and Polysorp and Maxisorp Immunosticks (Nunc, Denmark). In some cases the material was impregnated with chemoattractant alone; in other cases, the material was pretreated with glucose or gelatin.

It is also known that Phytophthora zoospores can detect electrical gradients and exhibit electrotaxis. The present inventors have found that zoospores of *P. cinnamomi* are strongly attracted to positively charged membranes such as Hybond-N+ (Amersham Australia Pty Ltd) and zeta-probe nylon membrane (Bio Rad Laboratories). Attraction of the zoospores to these latter membranes occurs in the absence of any applied chemoattractant.

SUMMARY OF THE INVENTION

According to one aspect of the present invention, there is provided a method for detecting motile organisms in a sample, which comprises contacting said sample with a solid support in a medium in which said organisms are motile, said solid support being an attractant or being treated with an attractant for said organisms; and subsequently detecting organisms attracted to said solid support.

Preferably, the attractant is one which creates a chemical or electric or electro-chemical gradient within the medium. Preferably, also said medium is a liquid medium.

In another aspect, this invention provides a solid support for use in a method as broadly described above, said solid support being an attractant or being treated with an attractant for the organisms. This solid support may be incorporated into a diagnostic or detection kit which further comprises means for detecting organisms attracted to the solid support.

DETAILED DESCRIPTION OF THE INVENTION

Central to the method of this invention is the use of a solid support, such as a dipstick, that attracts the organisms of interest. This is preferably achieved in one of two ways. The dipstick may be coated with a compound known to be a chemoattractant for the targeted organism. This compound will diffuse away from the dipstick and establish a gradient of the chemoattractant in the liquid medium. Alternatively or additionally, a support such as a membrane support that possesses an electrical charge may be used to establish an electrical gradient in the liquid medium.

Any suitable method may be used for detecting the targeted organism attracted to the solid support. By way of example, the organism may be detected by use of monoclonal antibodies specific for the targeted organisms. In the case of $P.$ $cinnamomi$, species-specific monoclonal antibodies are known (17,18), and such antibodies may be used for detection and immunological identification of this fungal species. The monoclonal antibodies are directed towards specific components of the encysted zoospore and preferably recognise antigens on the cyst surface. The assay is specific for *P. cinnamomi* and shows no cross-reactivity with other Phytophthora species, genera of Oomycetes or plant pathogenic fungi. The sensitivity, specificity and ease of use of the assay will enable widescale application in the forests and crops affected by this pathogen and offers considerable savings in both time and labour.

In general terms, the method of the present invention is based on the application of the phenomenon of chemotaxis and, with the selection of appropriate capture membranes, this can be augmented by electrotaxis to a positive charge. That both of these taxes can be used has implications for the success of the assay. Diffusion of a chemoattractant enables a "long-distance" (several millimeters), short term (minutes), chemical gradient to be established, while the presence of a positive charge in and around the immediate vicinity of the membrane serves as a "close-range", longer term (hours) attractant.

Zoospores of oomycetous fungi are attracted by a variety of chemical compounds including amino acids, sugars, alcohols, aldehydes and phenolic compounds (2,7,19,20,28). Attraction of *P. cinnamomi* zoospores to several phenolic acids and phytohormones has not been previously reported. In a similar assay, other phenolic compounds, especially the isoflavones, diadzein and genistein, were both potent and specific attractants of zoospores of *P. sojae* (28). Of the 65 compounds and mixtures tested in the present study, 32 attracted zoospores of *P. cinnamomi* at a concentration of 24 mM or less to some degree. The alcohols, amino acids and isovaleraldehyde were the most attractive substances. The present inventors have also demonstrated that the aspartic acid and glutamic acid can induce both attraction and encystment of zoospores of *P. cinnamomi* in a manner similar to that found for zoospores of *Py. aphanidermatum* (19). Aspartic acid is used as the preferred attractant because it was a potent attractor and induced encystment.

The sensitivity of the dipstick assay of the present invention has been determined to be as few as 40 zoospores $ml^{-1}$ in a conical flask. This level of sensitivity is similar to that of an immunoassay for zoospores in irrigation water (1) and detection of ascospores of *Venturia inequalis* (4), and greater than that of a chemiluminescence-based assay for bacteria in soil (30).

The immunoassay used by the present inventors routinely involved silver enhancement of colloidal gold-labelled secondary antibody. This detection system produced by an intense signal of high contrast that was easily distinguished by eye, hand-held lens or dissecting microscope. The cyst coat material which is immunologically distinct from material which aids in adhesion of cysts (15), spread out around the perimeter of the cyst during assay incubation and hence increased the amount and area of labelling and increased the signal.

In preliminary experiments (data not shown) in which soil was infested with *P. cinnamomi,* the colloidal gold-silver enhancement technique allowed cysts to be readily distinguished from adhering soil and organic particles. The possibility of confusion with other particles adhering to the dipstick membrane, however, was completely eliminated with an alkaline phosphatase-labelled secondary antibody with naphthol phosphate/fast red as the substrate and indicator dye. The pink-red colored cysts were easily distinguished from all other adherent matter. Fast blue, which gives an insoluble light-blue colored product, and bromochloroindoyl phosphate/nitroblue tetrazolium (BCIP/NBT), that gives an insoluble purple reaction product, have also been used to differentiate cysts of *P. cinnamomi* on dipsticks that have been used in soil samples.

The length of time used to run the routine assay was 3.4–4 h to maximize labelling and detection in the screening assays, however, for development into a diagnostic kit, assay time could be reduced considerably. In particular, use of alkaline phosphatase conjugated secondary antibody and fast dyes decreased the signal development time to only a few minutes. A biotin-streptavidin-based immunoassay also has the potential to both increase the signal and reduce assay time. With biotin-labelled secondary antibody and straptavidin-labelled with colloidal gold (15 nm), the silver enhancement time was cut to one third that when a gold labelled secondary antibody was used although with increased background signal (data not shown). Process time can also be greatly reduced by making the assay direct rather than indirect by using, for example, a colloidal gold-labelled primary antibody that can then be enhanced. Duration of the procedure was reduced with no loss in sensitivity when this technique was employed with a Cpa primary antibody conjugated to 10-nm gold.

Several immunologically based assays for the detection of plant pathogens are currently available in kit form, and several assays that use monoclonal antibodies as the detection system have been reported (9,27). Cross-reactivity however, has limited the use of many of these assays, which have immunogens based on whole cells or cell walls and soluble surface antigens. Similarly, the usefulness of commercial diagnostic tests for the detection of Phytophthora and *P. cinnamomi* in particular has been severely hampered by cross-reactivity both within the genus and to other closely related genera such as Pythium and Peronospora (1,3,23,29).

Further features of the method and other aspects of the present invention will be apparent from the detailed description in the following Example.

EXAMPLE 1

Materials and Methods

Fungal Isolates

The *P. cinnamomi* isolate (A2 mating type, 6BR, H1000) used throughout this work was originally isolated from the Brisbane Ranges, Victoria, Australia. Sources and culture conditions for all other isolates of Phytophthora and isolates of Pythium and Saprolegnia have been detailed (13) and have been assigned culture collection identification numbers (Table 1 in (13)).

Zoospore Production

Zoospores of *P. cinnamomi* were produced axenically (6) and zoospores of all other fungi were produced with the method of Dolan and Coffey (12). Numbers of zoospores in suspensions ranged from $1\times10^3$–$5\times10^5$ ml$^{-1}$.

Monoclonal Antibodies

Monoclonal antibodies (MAbs) from a previously described collection (17,18) were used. The MAbs were grouped according to labelling patterns on zoospores and cysts; Zt binds to the surface of the anterior, tinsel flagellum; Zg binds to a restricted area in the central groove and to mastigonemes on the anterior flagellum; Cpa binds to the cyst coat material; Lpv binds to the contents of large peripheral vesicles; Cpw binds to the cyst wall; ZCp binds to the surface of both zoospores and cysts; and Vsv and Gvv bind to the contents of ventral surface vesicles located around the groove region.

Chemotaxis Assay

A wide range of analytical-grade chemical compounds, including sugars, amino acids, phenolic compounds, alcohols, organic acids and plant hormones, were tested. The assay for determining the chemoattractiveness of compounds for zoospores of *P. cinnamomi* was modified from an agar-filled tube technique (20). A chemotaxis chamber was formed by attaching two 5-µl microcapillary tubes longitudinally, 13 mm apart, in the center of a glass microscope slide (25.4×72.6 mm) and then placing a glass coverslip (22×22 mm) over the capillary tubes to form an open-ended chamber (240 µl in volume). Zoospore suspension was carefully introduced into the chamber from a glass pipette. The test substance, dissolved in distilled water, was drawn into a 5-µl capillary tube and inserted 7 mm into one end of the chamber. A tube that contained distilled water alone was inserted into the opposite end of the chamber and served as the control in each test. Four slides were prepared for each test substance. Slides were immediately transferred to a humidity chamber that was then kept in the light at room temperature (approximately 25 C). After incubation for 20 min, slides were removed from the chamber and heated for 5 sec on a hotplate to immobilize the zoospores. Counts of zoospores within the capillary tubes were made from images produced from a videographic printer (Sony (Australia) Pty. Ltd., North Ryde, NSW, 2113) coupled to a monitor and video camera mounted on a Zeiss Photoscope III microscope. Zoospores were counted individually by an electronic colony counter (Manostat, New York, N.Y., USA). Mean number of zoospores in the test and control capillaries were calculated, and depending on the ratio of the number of zoospores in the capillary containing the attractant to the number of zoospores in the capilliary without attractant the test compounds were rated as not attractive (ratio of 1:1), weakly attractive (1:1.1–1.5), moderately attractive (1:1.6–2.5) or strongly attractive (1:>2.5) (Table 1). Tests were performed at least twice on each test substance.

Dipstick Design

In preliminary experiments, there was used a range of solid supports on which zoospores were able to encyst and adhere. Supports included plastic, glass, filter paper, an Immunostick (Nunc, Denmark), nitrocellulose membranes (plain nitrocellulose and supported nitrocellulose from Bio-Rad, North Ryde, NSW, 2113 and Hybond-C and Hybond Super-C from Amersham Australia Pty Ltd, North Ryde, NSW, 2113), nylon membranes (zeta-probe and zeta-probe GT, both positively charged, from Bio-Rad, and Hybond-N and Hybond-N+, the latter positively charged, from Amersham), and a polyvinylidene difluoride (PVDF) membrane from Bio-Rad. These supports were variously treated for use in several assay types (Table 2). In some assays, an attractant was added to the membrane square which, in several tests, was attached to one end of a plastic support by clear nail varnish. In other assays, the attractant was added to filter paper strips or mixed with gelatin, poly-L-lysine or glucose and applied to the solid support. The effectiveness of the dipstick format in attracting and capturing the zoospores was assessed by counting the number of cysts that had adhered to the dipsticks after a 30-min incubation in a zoospore suspension ($10^4$ ml$^{-1}$). Dipsticks that did not contain attractant served as controls.

Dipstick Immunoassay

Several direct and indirect immunoassays were assessed in preliminary experiments. In initial tests, the presence of cysts on the dipstick was tested with an alkaline phosphatase- or horseradish peroxidase-conjugated secondary antibody enzyme reaction to produce a colored solution, but these assays were successful only when high numbers of cysts (500–1000) were attached to the membrane (data not shown). Methods based on the formation of an insoluble, colored precipitate on and around the cysts were far superior. An indirect immunoassay with a colloidal gold (10 nm)-labelled secondary antibody (AuroProbe™ BL plus GAM IgG+IgM (H+L), Amersham) and subsequent silver enhancement (IntenSE™ BL silver enhancement kit, Amersham) was used routinely in all subsequent experiments. During development of the method, assays were run in 96-well ELISA trays and the total assay time was 3.5–4 h. The time taken for the assay was reduced to less than 45 min without loss of sensitivity by reducing incubation times and by increasing the concentrations of the primary and secondary antibodies.

For the routine assay a dipstick was placed in 200 µl of zoospore suspension for 30 min and transferred to 250 µl of 5% skim milk (Carnation, Sydney, NSW, 2000) in Tris-buffered saline, (TBS) pH 7.4, with 0.1% gelatin for 15 min. The dipstick was washed twice for 3 min in 250 µl TBS containing 0.8% bovine serum albumin (Sigma Chemical Co., Castle Hill, NSW, 2154) (TBS/BSA) and placed into 200 µl of genus- or species-specific monoclonal antibody appropriately diluted in TBS/BSA. After incubation for 45 min, the dipstick was washed twice for 3 min in 250 µl TBS/BSA and placed into 200 µl of gold-labelled goat anti-mouse IgG+IgM (H+L) for 45 min. The dipstick was then washed once in 250 µl TBS/BSA for 3 min, once in 250 µl TBS for 3 min, and in 250 µl of distilled water for 1 min. The dipstick then was transferred to 250 µl of silver enhancement reagent. Within 60–70 min, an intense black precipitate formed on and around cysts, which had bound the primary antibody. The reaction was stopped by immersing the dipstick in distilled water for 1–2 min. The dipstick was then air-dried, and cysts were observed unmagnified or with a 10X hand lens. Dipsticks were critically examined with a stereo dissecting microscope with zoom optics (maximum magnification 67.5X) and incident illumination. All steps in the protocol were conducted in a laboratory at room temperature under constant lighting conditions. In assays for which counts of the total number of cysts on each dipstick were required, the procedure used for counting cysts in the chemotaxis chambers was followed. Dipsticks were attached to microscope slides with adhesive tape and illuminated from above with a dissecting microscope light source.

Application of the Chemoattractant

Aspartic acid or glutamic acid were dissolved in distilled water at 95 C. A 1-µl aliquot of a suitably diluted solution of the amino acid was placed in the center of the membrane square. The dipsticks were then used immediately or stored desiccated. To test the effectiveness of these two compounds after application to the dipstick membrane, dipsticks were incubated in a zoospore suspension for 30 min, and cysts were counted as described above.

Monoclonal Antibody Screening

Twenty-four MAbs, selected from the immunofluorescence assay as potentially diagnostic from an original collection of 35 MAbs (13), were screened for the ability to bind to cysts in the dipstick assay. Affinity purified antibodies (1 or 10 $\mu$g ml$^{-1}$) or hybridoma supernatants (neat or 50% dilution in TBS/BSA) were used in the indirect immunoassay and each was scored after silver enhancement of the secondary probe relative to a non-immune mouse IgG (NIM) negative control (10 $\mu$g ml$^{-1}$) for their ability to bind to cysts that were attached to the dipstick membrane and to produce a visible precipitate. MAbs were tested on duplicate dipsticks with *P. cinnamomi* (6BR, H1000) cysts.

Cross-reactivity of Phytophthora and Related Genera

Cross-reactivity of the MAbs with cysts of isolates of Phytophthora Phythium or Saprolegnia was tested with the dipstick immunoassay. The Cpa MAbs (Cpa-2, 1 $\mu$g ml$^{-1}$ of the purified MAb; Cpa-3, 25% dilution of hybridoma supernatant and Cpa-7, 50% dilution of hybridoma supernatant) and ZCp-2 (50% dilution of hybridoma supernatant) and Cpw-4, (10 $\mu$g ml$^{-1}$ of purified MAb) were tested. NIM (10 $\mu$g ml$^{-1}$) was used as the negative control for each isolate. All MAbs were diluted in TBS/BSA. MAb Vsv-1, which recognises an antigen within the ventral surface vesicles of zoospores in each of the genera, was used as a check for the presence of cysts of Pythium and Saprolegnia on the dipstick membrane since cysts of these genera were not labelled by the MAbs tested. The dipsticks were joined in strips of 12 so that they could be used in a 96-well ELISA plate assay.

Sensitivity of the Dipstick Assay

Three procedures were compared and used to determine the dipstick assay sensitivity. A dilution series of zoospores from an initial concentration of $10^4$ zoospores ml$^{-1}$ was used for each. In the first procedure, the zoospore suspension was diluted with distilled water to a range of concentrations in a total volume of 12 ml and was added to a 10 ml Erlenmeyer flask so that the surface of the zoospore suspension was approximately half-way up the neck (12 mm internal diameter) of the flask. In the second procedure, 10 ml of zoospore suspension was dispensed into small glass Petri dishes (40 mm diameter). A single dipstick was placed, membrane side down, on the surface of the zoospore suspension in each flash or Petri dish. In a third procedure, dipsticks were used in an ELISA tray assay in which zoospores were diluted with distilled water to form a dilution series. Dipsticks were placed vertically into 200 $\mu$l of zoospore suspension within the well of the tray. After incubation for 30 min in the zoospore suspensions, dipsticks were removed and subjected to immunoassay. Cysts on the dipstick membrane were counted as described above.

RESULTS

The results are set out in Tables 1–4 as follows:

Table 1: Relative attractiveness of compounds for zoospores of *P. cinnamomi* determined using an assay in which the cells swim into a capillary from which the test compound is diffusing.

Table 2: The effectiveness of various solid supports, assays, coatings and chemoattractants for the capture and assay of zoospores of *P. cinnamomi*.

Table 3: Comparison of amino acids (1 mM) in the chemotaxis assay for attractiveness to *P. cinnamomi* zoospores.

Table 4: Screening results obtained in the dipstick assay to determine the reaction of 24 monoclonal antibodies with differing binding characteristics for labelling of cysts of *P. cinnamomi*.

Selection of Chemoattractant(s)

Compounds that were chemotactically attractive to zoospores of *P. cinnamomi* were identified in the "swim-in" assay (Table 1). Many of the compounds tested caused rapid accumulation of zoospores within the capillary tubes. The compounds included those known to occur in the rhizosphere, root exudates, and roots of many plant species e.g. (8,25). Of the compounds tested, several amino acids, phenolic compounds and isovaleraldehyde were highly attractive. The amino acids aspartic acid and glutamic acid, were especially attractive (Table 3). Some compounds, including pectin, syringic acid, abscisic acid, aspartic acid and glutamic acid, also caused encystment. Sugars were generally not attractive except at relatively high concentrations (>100 mM, data not shown). Preliminary experiments with several of the compounds run in dilution series demonstrated that there was a concentration for each compound (usually >100 mM) above which zoospores were repelled or encysted rapidly and a concentration below which zoospores were not attracted. For example, concentrations of aspartic and glutamic acids that caused the greatest accumulation of zoospores within the capillary tubes differed and was 0.1 mM for aspartic acid (L- or D-configuration) and 1 mM for glutamic acid. On the basis of their attractiveness and encystment-inducing properties, aspartic and glutamic acids, arginine, pectin, and ethanol were chosen for use in development of the dipstick assay.

Dipstick Format

Zoospores were attracted to and encysted upon all the solid supports used (Table 2). The presence of an attractant absorbed into a membrane, mixed with the coating substance or dried to the support surface increased the number of cysts bound to the support compared with controls that did not contain attractant. Cyst numbers were higher on the nitrocellulose and nylon membranes treated with attractant than on other support types and coatings. Coated supports such as the Immunostick, glass slides and the plastic dipstick attracted zoospores, but the coating material usually did not bind well and was lost after several washes. This made the coatings inappropriate for use in an immunoassay. In contrast, cysts adhered well to the membrane surfaces and were not removed by washing.

The most successful and useful format was the plastic dipstick (5 mm×20 mm) with a square (5 mm×5 mm) of nitrocellulose or nylon membrane glued to one end. A variety of membrane types were tried but the nylon membranes, which are more hydrophilic than nitrocellulose, enabled more even dispersal and rapid absorption of the water drop containing the dissolved attractant. The PVDF membrane, although used successfully by others (9), was unsuitable because it must be wetted with methanol before use. Positively charged nylon membranes attracted zoospores in greater numbers with or without added chemoattractant than neutral membrane. The zeta-probe nylon membrane, which carries a high-density quaternary amine charge, was especially attractive.

These plastic dipsticks with attached membrane had several advantages over the other supports and coatings. They could be used vertically in or horizontally on a zoospore suspension and could be used in 96-well ELISA trays either as single sticks or, when correctly aligned on a length of adhesive tape, in strips of up to twelve. The use of multiple dipstick strips enabled the processing of many samples simultaneously and considerably eased the logistics of the immunoassay.

Monoclonal Antibody Screening

There was no labelling by MAbs of the Zt group of *P. cinnamomi* (6BR, H1000) cysts that had adhered to the dipstick membrane (Table 4). There were very small localized areas of labelling with each of the Zg MAbs (possible labelling of the water expulsion vacuole, but these could be seen only under high-power magnification (>100X). All the Lpv MAbs gave weak to very weak, diffuse labelling patterns. In contrast, seven of the Cpa MAbs reacted moderately or strongly with material coating the cyst surface. Three of the Cpa Mabs (Cpa-5, Cpa-8 and Cpa-12) showed none or only weak labelling. The Cpw-4 and ZCp-2 MAbs reacted moderately and the Gvv MAb only weakly in the assay.

Five MAbs were selected based on the intensity of labelling of cysts in the dipstick assay and on supplementary information from immunofluorescence and ELISA studies (13); MAbs Cpa-2, Cpa-3 and Cpa-7 (putative species-specific) and Cpw-4 and ZCp-2 (putative genus-specific). These MAbs were used in further studies to test for specificity in the dipstick assay.

Screening Phytophthora and Related Genera

Forty-four isolates of *P. cinnamomi* including 15 A1 mating type and 29 A2 mating type, obtained from throughout Australia and including isolates from Papua New Guinea and Japan, 21 species of varieties of Phytophthora encompassing 75 isolates, 11 species of Pythium encompassing 13 isolates and three species of Saprolegnia (one isolate each) were tested against the five selected MAbs with the dipstick assay. All three Cpa MAbs labelled cysts of the *P. cinnamomi* isolates but did not label any cysts from isolates of the other Phytophthora species or varieties. In contrast, MAbs Cpw-4 and ZCp-2 labelled all Phytophthora isolates. Slight variation occurred among the *P. cinnamomi* isolates in labelling intensity of the cysts, but no difference occurred between A1 and A2 mating types. The putative species-specific MAbs labelled cysts more strongly than the putative genus-specific MAbs.

MAbs Cpa-3 and Cpa-7 did not label any cysts from the isolates of Pythium and Saprolegnia tested. MAb Cpa-2 did, however, cross-react weakly with *Pythium aphanidermatum, Py. butleri, Py. debaryanum, Py. irregulare* and *S. declina*. MAb ZCp-2 reacted weakly with *Py. debaryanum* and *Py. irregulare*. MAb Cpw-4 reacted weakly with *Py. middletonii*. MAb Vsv-1, which labels the contents of ventral surface vesicles, reacted with all isolates of Pythium and Saprolegnia.

Dipstick Assay Sensitivity

The shape of the container holding the zoospore solution influenced the number of cysts found on the dipstick membrane. Over the range of dilutions of the zoospore suspension more cysts were found on dipsticks used in the conical flask assay than the Petri dish or ELISA plate assays. The sensitivity of the dipstick assay was determined from a dilution series as the highest dilution of zoospores that could be detected. For the conical flask assay, 40 zoospores $ml^{-1}$ was the lowest concentration at which one or more cysts were found on the dipstick membrane after the 30 min incubation period. Minimum detection limits were 156 and 312 zoospores $ml^{-1}$ for the Petri dish and ELISA plate assays, respectively. Results from the ELISA plate assay are, however, not directly comparable with those of the other two assays because the dipsticks were placed vertically in the zoospore solution. A single cyst attached to the dipstick membrane was the minimum required for a positive identification although in practice probably no fewer than 5–10 cysts per membrane would be the minimum necessary to be confident of an identification.

TABLE 1

Relative attractiveness of compounds for zoospores of *P. cinnamomi* determined by a chemotaxis assay.

| Compound (molarity) | RA | Compound (molarity) | RA | Compound (molarity) | RA |
|---|---|---|---|---|---|
| Sugars (10 mM) | | Amino acids (1 mM) | | Organic acids (10 mM) | |
| D-Mannose | − | L-Aspartic acid | +++* | Maleic | + |
| D-Xylose | − | D-Aspartic acid | +++ | L-Malic | + |
| D-Ribose | − | L-Methionine | − | Citric | +* |
| D-Fructose | − | D-Methionine | − | Succinic | − |
| D-Lactose | − | L-Glutamic acid | +++* | Fumaric | + |
| D-Glucose | − | L-Arginine | ++ | L-Ascorbic | ++ |
| Sucrose | − | Guanidine | + | Valeric | + |
| D-Galactose | − | Glycine | − | Isovaleric | + |
| L-Fucose | − | L-Cysteine | + | Folic | − |
| D-Cellobiose | − | L-Lysine | − | Acetic | − |
| L-Rhamnose | − | L-Leucine | − | | |
| L-Arabinose | − | L-Phenylalanine | − | Pectin and derivatives | |
| | | L-Tyrosine | − | D-Galacturonic acid (100 ug/ml) | − |
| Phenolics (10 mM) | | | | Polygalacturonic acid (100 ug/ml) | + |
| Caffeic acid | +* | Alcohols (25 mM) | | Pectin (100 ug/ml) | ++* |
| Hydroxy-benzoic acid | − | Ethanol | +++ | | |
| Ferulic acid | ++ | Methanol | ++ | Aldehyde (1 mM) | |
| Syringic acid | +* | Isopropanol | +++ | Isovaleraldehyde | +++ |
| Gallic acid | −* | | | | |
| Gentisic acid | +* | Phytohormones (10 mM) | | Miscellaneous | |
| p-Coumaric acid | − | Kinetin | − | Casein 100 ug/ml | −* |
| Vanillin | + | Benzyl-aminopurine | − | Casein hydrolysate 100 ug/ml | + |
| Coumarin | − | Iso-pentenyladenine | − | | |
| Phloroglucinol | − | +/− Abscisic acid | +* | V8 juice (20%) | + |
| Rutin | − | Gibberellic acid (GA3) | − | V8 broth (5%) | + |
| Myrcetin | − | Indolbutyric acid | +* | | |
| Kaempferol | − | Napthalene acetic acid | +* | Gelatine (10%) | ++ |

RA-Relative attractiveness
−, compound not attractive
+, weakly attractive
++, moderately attractive
+++, highly attractive
*, cause encystment

TABLE 2

Effectiveness of various solid supports, assays, coatings and chemoattractants for the capture and assay of zoospores of *P. cinnamomi*.

| Solid support | Assay format | Coating | Test compound | Ratio |
|---|---|---|---|---|
| Nitrocellulose membrane | Square (5 × 5 mm) floated on zoospore suspension | Nc | Aspartic acid | ++ |
| | | Nc | Arginine | + |
| | | Nc | Glutamic acid | +++ |
| | | Nc | V8 broth | + |
| | | Nc | Pectin | ++ |
| | Strips (2 × 10 mm long) in chemotaxis chamber | Nc | Aspartic acid | ++ |
| | | Nc | Glutamic acid | +++ |
| | | Nc | Ethanol | +++ |
| | Strips (5 × 10 mm long) in ELISA tray | Nc | Aspartic acid | + |
| | | Nc | Glutamic acid | ++ |
| | | Nc | Pectin | +++ |
| | | Nc | Ethanol | ++ |
| Immunostick | Immersed in zoospore suspension | Nc | Aspartic acid | + |
| | | Nc | Glutamic acid | + |
| | | Nc | Pectin | + |
| | | 5% glucose | Aspartic acid | + |
| | | 5% glucose | Glutamic acid | ++ |
| | | 5% glucose | Pectin | + |
| | | 10% gelatin | Aspartic acid | + |
| | | 10% gelatin | Glutamic acid | ++ |
| | | 10% gelatin | Pectin | ++ |
| | | Poly-L-Lysine | Aspartic acid | + |
| | | Poly-L-Lysine | Glutamic acid | +++ |
| | | Poly-L-Lysine | Pectin | ++ |
| Plastic dipstick (5 × 20 mm long) | ELISA tray | 10% gelatin | Glutamic acid | + |
| | | Poly-L-Lysine | Glutamic acid | + |
| Plastic dipstick (5 × 20 mm long) | Nitrocellulose membrane (5 × 5 mm) | Nc | Aspartic acid | +++ |
| | | Nc | Glutamic acid | +++ |
| | Nylon membrane (5 × 5 mm) | Nc | Aspartic acid | +++ |
| | | Nc | Glutamic acid | +++ |
| | Nylon membrane (5 × 5 mm) | Nc | No attractant | +++ |
| Filter paper | Strips (2 × 10 mm long) in chemotaxis chamber | Nc | Aspartic acid | ++ |
| | | Nc | Glutamic acid | ++ |
| | | Nc | Ethanol | ++ |
| Glass microscope slide | Immersed in zoospore suspension | 10% gelatin | Aspartic acid | ++ |

Ratio is the number of zoospores on the solid support treated with the attractant divided by number of zoospores on the solid support without attractant where + = ratio of 1.1–1.5, ++ = 1.6–2.5, and +++ = >2.5, Nc = not coated.

TABLE 3

Comparison of amino acids (1 mM) in the chemotaxis assay for attractiveness to *P. cinnamomi*

| | Number of zoospores in capillaries | | |
|---|---|---|---|
| Amino acid | Control | +amino acid | Ratio |
| L-Aspartic | 24.6 ± 11.2 | 128.2 ± 32.0 | 1:5.2*** |
| D-Aspartic | 30.2 ± 7.7 | 116.8 ± 18.3 | 1:39*** |
| L-Methionine | 26.6 ± 11.8 | 41.4 ± 15.0 | 1:1.6 |
| D-Methionine | 102.4 ± 10.2# | 99.4 ± 21.3# | 1:1.0 |
| L-Glutamic | 20.0 ± 7.3 | 78.2 ± 18.8 | 1:3.9* |
| L-Arginine | 32.8 ± 6.4 | 147.4 ± 37.1 | 1:45*** |

Mean and standard error of the mean of four replicates in two separate experiments are shown.
Data are counts from one field of view (×10 objective) or from two (#) fields of view,
Ratio calculated as number of zoospores in the capillaries containing the amino acid divided by the number in capillaries without amino acid.
*, significantly different from controls, $P < 0.1$, , $P < 0.05$, *, $P < 0.01$

TABLE 4

Results of screening 24 MAbs for effectiveness of labelling of *P. cinnamomi* cysts in the dipstick assay.

| MAb | Reaction |
|---|---|
| Zt-1 | − |
| Zt-2 | − |
| Zg-1 | − |
| Zg-2 | − |
| Zg-3 | − |
| Zg-4 | − |
| Cpa-2 | ++ |
| Cpa-3 | +++ |
| Cpa-4 | ++ |
| Cpa-5 | + |
| Cpa-6 | ++ |
| Cpa-7 | +++ |
| Cpa-8 | − |
| Cpa-9 | ++ |
| Cpa-10 | ++ |
| Cpa-12 | +/− |

TABLE 4-continued

Results of screening 24 MAbs for effectiveness of
labelling of *P. cinnamomi* cysts in the dipstick assay.

| MAb | Reaction |
|---|---|
| Lpv-1 | + |
| Lpv-2 | +/− |
| Lpv-3 | +/− |
| Lpv-4 | +/− |
| Lpv-5 | +/− |
| Cpw-4 | ++ |
| ZCp-2 | ++ |
| Gvv | + |

−, no labelling
+/−, trace
+, weak
++, moderate
+++, strong

EXAMPLE 2

Materials and Methods

Tests in the Glasshouse/Constant Environmental Cabinets

Tests have been carried out in constant environment chambers to determine whether the dipstick assay is effective under glasshouse and field conditions and is specific for *P. cinnamomi*, in the presence of spores of other Phytophthora and Pythium species. Tests have involved the inoculation of several plant species (*Eucalyptus sieberi, Pinus radiata, Lycopersicon esculentum* and *Banksia serrata*) with isolates of *Phytophthora cinnamomi* A1, *P. citricola, P. nicotianae var nicotianae, P. cryptogea* and two Pythium species, *Pythium aphanidermatum* and *Py. irregulare*. These isolates have been used singly or in combination with and without the addition of *P. cinnamomi* A2.

Reisolation of *P. cinnamomi* A2 has used several different methods. All experiments have used a baiting assay (*Eucalyptus sieberi* cotyledons/or pine needles) to check and confirm results of the dipstick assay. Baits are plated onto selective media containing antibiotics which inhibit the growth of fungi (other than Phytophthora and Pythium) and bacteria and the inoculum present confirmed by traditional taxonomic means. In addition, dipsticks have been plated onto selective media to prove the presence of both spores of *P. cinnamomi* and the other Phytophthora and Pythium species in the samples taken. In some experiments aliquots of the soil slurry made from the sample taken have been plated onto selective media to again confirm the presence of the isolates of interest.

All the above procedures for reisolating *P. cinnamomi* work, especially the dipstick and baiting assays. Plating of dipsticks onto selective media has been less reliable (probably because only one dipstick per sample is sampled) for reisolation of *P. cinnamomi* but has been extremely useful for proving that motile spores of the other species are being produced and are attaching to the membrane on the dipstick. The soil slurry technique, also useful for estimating amounts of fungal material in the sample suffers from contamination by fungi and bacteria which are not inhibited by the selective media.

The dipstick assay has proven extremely reliable for detection of *P. cinnamomi* under the controlled conditions used. There are only a small number of cases where the dipstick has failed to pick up *P. cinnamomi* when the baiting assay has been positive. It should be noted that there are also examples of the reverse, i.e. dipstick positive, baiting negative.

B. Tests on Soil Collected in the Field

The critical test of the dipstick assay is whether it has the ability to detect *P. cinnamomi* in field soils. Data now exists to show that the assay works in different soil types from several sites around Australia.

The present inventors have used similar isolation and confirmation procedures to those used in the controlled experiments, i.e. plating of baits onto selective media, plating of dipsticks onto selective media and isolation from soil slurries. In addition, identifications from field soil have been rigorously confirmed by isolating putative Phytophthora species, bringing them into pure culture, inducing them to produce zoospores and then running the dipstick assay on the pure zoospore cultures.

The dipstick assay has been completely reliable for identifying *P. cinnamomi* in the field soils. There have been no cases to date where there is not agreement between baiting and traditional methods of isolation and the dipstick assay.

C. Sensitivity of the Dipstick Assay

In the laboratory experiments previously described, it has been determined that the dipstick assay is capable of detecting as few as 40 zoospores per milliliter. In tests where plants grown in soil in pots have been inoculated with a zoospore dilution series (plants used have been *Pinus radiata, Lycopersicon esculentum,* and *Banksia serrata*) the dipstick assay and the cotyledon baiting assay are capable of detecting the presence of *P. cinnamomi* after the addition of 3000 zoospores per pot. In some instances the dipstick assay has detected the presence of *P. cinnamomi* after the addition of only 300 zoospores per pot.

It will be appreciated that the above Examples are included by way of illustration, and not limitation, of the invention as broadly described herein, and that many modifications and variations may be made without departing from the spirit and scope of the invention.

REFERENCES

1. Ali-Shtayeh, M. S., MacDonald, J. D. and Kabashima, J. (1991). A method for using commercial ELISA tests to detect zoospores of Phytophthora and Pythium species in irrigation water. *Plant Dis.* 75:305–311.
2. Allen, R. N. and Newhook, F. J. (1973). Chemotaxis of zoospores of *Phytophthora cinnamomi* to ethanol in capillaries of soil pore dimensions. *Trans. Br. mycol. Soc.* 61:287–302.
3. Benson, D. M. (1991). Detection of *Phytophthora cinnamomi* in Azalea with commercial serological assay kits. *Plant Dis.* 75:478–482.
4. Berkett, L. P., Gotleib, A. R. and Bergdahl, J. A. (1992). Development of an antibody-based diagnostic kit to detect mature *Venturia inequalis* ascospores. *Arch. Microbiol.* 55:66–77. (Abstract)
5. Bossi, R. and Dewey, F. M. (1992). Development of monoclonal antibody-based immunodetection assay for *Botrytis cinerea. Plant Pathol.* 41:472–482.
6. Byrt, P. and Grant, B. R. (1979). Some conditions governing zoospore production in axenic cultures of *Phytophthora cinnamomi* Rands. *Aust. J. Bot.* 27:103–115.
7. Cameron, J. N. and Carlile, M. J. (1978). Fatty acids, aldehydes and alcohols as attractants for zoospores of *Phytophthora palmivora. Nature* 271:448–449.
8. Curl, E. A. and Truelove, B. (1986). The Rhizosphere. Springer-Verlag, Berlin.
9. Dewey, F. M. (1992). Detection of plant-invading fungi by monoclonal antibodies. PP 47–62 in: Techniques for the Rapid Detection of Plant Pathogens. J. M. Duncan and L. Torrance, eds. Blackwell Scientific Publications, Oxford.

10. Dewey, F. M., MacDonald, M. M. and Phillips, S. I. (1989). Development of monoclonal-antibody-ELISA, DOT-BLOT and -DIP-STICK immunoassays for *Humicola langinosa* in rice. *J. Gen. Microbiol.* 135:361–374.
11. Dewey, F. M., MacDonald, M. M., Phillips, S. I. and Priestley, R. A. (1990). Development of monoclonal-antibody-ELISA and -DIP-STICK immunoassays for *Penicillium islandicum* in rice grains. *J. Gen. Microbiol.* 136:753–760.
12. Dolan, T. E. and Coffey, M. D. (1986). Laboratory screening techniques for assessing resistance of four avocado rootstocks of *Phytophthora cinnamomi, Plant Dis.* 70:115–118.
13. Gabor, B. K., O'Gara, E. T., Philip, B. A., Horan, D. P. and Hardham, A. R. (1993). Specificities of monoclonal antibodies to *Phytophthora cinnamomi* in two rapid diagnostic assays. *Plant Dis.* (in Press).
14. Greenhalgh, F. C. (1978). Evaluation of techniques for quantitative detection of *Phytophthora cinnamomi*. *Soil Biol. Biochem.* 10:257–259.
15. Gubler, F. and Hardham, A. R. (1988). Secretion of adhesive material during encystment of *Phytophthora cinnamomi* zoospores, characterized by immunogold labelling with monoclonal antibodies to components of peripheral vesicles. *J. Cell Sci.* 90:225–235.
16. Hampton, R., Ball, E. and DeBoer, S. (1990). Serological Methods for Detection and Identification of Viral and Bacterial Plant Pathogens. APS Press, St. Paul., Minn.
17. Hardham, A. R., Gubler, F., Duniec, J. and Elliott, J. (1991). A review of methods for the production and use of monoclonal antibodies to study zoosporic plant pathogens. *J. Microsc.* 162:305–318.
18. Hardham, A. R., Suzaki, E. and Perkin, J. L. (1986). Monoclonal antibodies to isolate-, species- and genus-specific components on the surface of zoospores and cysts of the fungus *Phytophthora cinnamomi*. *Can. J. Bot.* 64:311–321.
19. Jones, S. W., Donaldson, S. P. and Deacon, J. W. (1991). Behaviour of zoospores and zoospore cysts in relation to root infection by *Pythium aphanidermatum*. *New Phytol.* 117:289–301.
20. Khew, K. L. and Zentmyer, G. A. (1973). Chemotactic response of zoospores of five species of Phytophthora. *Phytopathology* 63:1511–1517.
21. Kricka, L. J. and Thorpe, G. H. G. (1986). Immobilized enzymes in analysis. *Trends in Biotech.* 4:253–258.
22. MacDonald, J. D. and Duniway, J. M. (1979). Use of fluorescent antibodies to study the survival of *Phytophthora megasperma* and *P. cinnamomi* zoospores in soil. *Phytopathology* 69:436–441.
23. MacDonald, J. D., Stites, J. and Kabashima, J. (1990). Comparison of serological and culture plate methods for detecting species of Phytophthora, Pythium, and Rhizoctonia in ornamental plants. *Plant Dis.* 74:655–659.
24. Malajczuk, N., McComb, A. J. and Parker, C. A. (1975). An immunofluorescence technique for detecting *Phytophthora cinnamomi* Rands. *Aust. J. Bot.* 23:289–309.
25. Malajczuk, N. and McComb, A. L. (1977). Root exudates from *Eucalyptus calophylia* R. Br. and *E. marginata* Donn. ex Sm. seedlings and their effect on *Phytophthora cinnamomi* Rands. *Aust. J. Bot.* 25:501–514.
26. Miller, S. A., Grothaus, G. D., Peterson, F. P., Rittenburg, J. H., Plumley, K. A. and Lankow, R. K. 91987). Detection and monitoring of turfgrass pathogens by immunoassay. *Amer. J. Bot.* 55:66–77.
27. Miller, S. A. and Martin, R. R. (1988). Molecular diagnosis of plant disease. *Annu. Rev. Phytopath.* 26:409–432.
28. Morris, P. F. and Ward, E. W. B. (1992). Chemoattraction of zoospores of the soybean pathogen, *Phytophthora sojae*, by isoflavones. *Physiol. Mol. Pl. Path.* 40:17–22.
29. Pscheidt, J. W., Burket, J. Z., Fisher, S. L. and Hamm, P. B. (1992). Sensitivity and clinical use of Phytophthora-specific immunoassay kits. *Plant Dis.* 76:928–932.
30. Schloter, M., Bode, W., Hartmann, A. and Beese, F. (1992). Sensitive chemoluminescence-based immunological quantitation of bacteria in soil extracts with monoclonal antibodies. *Soil Biol. Biochem.* 24:399–403.
31. Shearer, B. L. and Tippett, J. T. (1989). Jarrah Dieback: The Dynamics and Management of *Phytophthora cinnamomi* in the Jarrah (*Eucalyptus marginata*) Forest of South-western Australia. Department of Conservation and Land Management, Como, Wash.
32. Snowden, K. and Hommel, M. (1991). Antigen detection using dipsticks and colloidal dyes. *J. Immuno. Methods* 140:57–65.
33. Tsao, P. H. (1983). Factors affecting isolation and quantitation of Phytophthora from soil. PP 219–236 in: Phytophthora. Its Biology, Taxonomy, Ecology, and Pathology. D. C. Erwin, S. Bartnicki-Garcia and P. H. Tsao, eds. American Phytopathological Society. St. Paul, Minn.
34. Weste, G. and Marks, G. C. (1987). The biology of *Phytophthora cinnamomi* in Australasian forests. *Annu. Rev. Phytopath.* 25:207–228.
35. Wils, R. T. (1993). The ecological impact of *Phytophthora cinnamomi* in the Stirling Range National Park, Western Australia. *Aust. J. Ecol.* 10:55–66.
36. Zentmyer, G. A. (1980). *Phytophthora cinnamomi* and the Diseases it Causes. The American Phytopathological Society, St. Paul, Minn.

We claim:

1. A method for detecting motile fungal zoospores without the detection of non-motile zoospores in a sample, which comprises contacting said sample with a solid support in a medium and under conditions in which said organisms are motile, said solid support being in the form of a dipstick which is an attractant or is treated with an attractant for said fungal zoospores wherein said attractant attracts said fungal zoospores by chemotaxis or electrotaxis or by the combination of chemotaxis and electrotaxis so that said motile fungal zoospores move through said medium to said solid support;

and subsequently detecting fungal zoospores attracted and adhered to said solid support.

2. A method according to claim 1, wherein fungal zoospores attracted to said solid support are detected by immunoassay.

3. A method according to claim 1, wherein said motile fungal zoospores are zoospores of *Phytophthora cinnamomi* and said solid support is treated with an attractant for said zoospores.

4. A method according to claim 3, wherein said attractant is selected from the group consisting of L-aspartic acid, D-aspartic acid, glutamic acid, arginine, pectin and ethanol.

5. A method according to claim 1 wherein said motile fungal zoospores are zoospores of *Phytophthora cinnamomi* and said solid support comprises an attractant for said zoospores.

6. A method according to claim 5, wherein said attractant is selected from nitrocellulose and nylon membranes.

7. A method according to claim 6, wherein said membrane is positively charged.

8. A method according to claim 3, wherein zoospores of *P. cinnamomi* attracted to said solid support are detected by immunoassay utilising a species-specific anti-*P. cinnamomi* monoclonal antibody.

9. A method according to claim 8 wherein said species-specific monoclonal antibody binds to antigen on the surface of *P. cinnamomi* cysts.

10. A solid support for use in the detection of motile fungal zoospores in a sample, said solid support being in the form of a dipstick which is an attractant or is treated with an attractant for said fungal zoospores wherein said attractant attracts said fungal zoospores by electrotaxis or by the combination of chemotaxis and electrotaxis.

11. A solid support according to claim 10, which is treated with an attractant selected from the group consisting of aspartic acid, glutamic acid arginine, pectin and ethanol.

12. A solid support according to claim 10, wherein said attractant is selected from nitrocellulose and nylon membrane.

13. A solid support according to claim 12, wherein said membrane is positively charged.

14. A kit for detecting motile fungal zoospores in a sample, which comprises
    (i) a solid support according to claim 10 and
    (ii) means for detecting fungal zoospores attracted to said solid support.

15. A kit according to claim 14, wherein said detecting means comprises means for performing an immunoassay.

16. A kit according to claim 15, wherein said means for performing an immunoassay comprises antibody binding to said fungal zoospores and reporter means for detecting said bound antibody.

17. A kit according to claim 14 for detecting zoospores of *P. cinnamomi* in a sample, wherein said detecting means comprises species-specific anti-*P. cinnamomi* monoclonal antibody.

18. A kit according to claim 17, wherein said species-specific monoclonal antibody binds to antigen on the surface of *P. cinnamomi* cysts.

19. The method of claim 5 wherein zoospores of *P. cinnamomi* attracted to said solid support are detected by immunoassay utilizing a species-specific anti-*P. cinnamomi* monoclonal antibody.

20. The method of claim 19 wherein said species-specific monoclonal antibody binds to antigen on the surface of *P. cinnamomi* cysts.

* * * * *